United States Patent [19]

Jevne et al.

[11] 4,156,095

[45] May 22, 1979

[54] PREPARATION OF $C_{21}$ DICARBOXYLIC ACID

[75] Inventors: Allan H. Jevne, Anoka, Minn.; Gerald L. Schwebke, Grafton, Wis.

[73] Assignee: Henkel Corporation, Minneapolis, Minn.

[21] Appl. No.: 847,375

[22] Filed: Oct. 31, 1977

[51] Int. Cl.² ............................................. C07C 51/00
[52] U.S. Cl. .................................................. 562/509
[58] Field of Search ................... 260/514 K; 560/127; 562/509

[56] References Cited

U.S. PATENT DOCUMENTS

| | | | |
|---|---|---|---|
| 3,753,968 | 8/1973 | Ward | 260/97.6 |
| 3,842,119 | 10/1974 | Bills | 260/408 |

OTHER PUBLICATIONS

Ishigami et al., Yakagaku 2Z 368 (1973).

*Primary Examiner*—Robert Gerstl
*Attorney, Agent, or Firm*—Patrick J. Span; Elizabeth Tweedy

[57] ABSTRACT

A method of preparing a $C_{21}$ dicarboxylic acid using crystalline clay as a catalyst.

4 Claims, No Drawings

PREPARATION OF $C_{21}$ DICARBOXYLIC ACID

This invention relates to a method of making a dicarboxylic acid using a crystalline type clay as catalyst. More particularly, this invention relates to a method of making a dicarboxylic acid containing twenty-one carbon atoms having the structural formula:

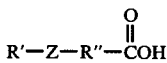

where R' is a monovalent straight chain aliphatic hydrocarbon radical containing 2 to 6 carbon atoms, R" is a divalent straight chain aliphatic hydrocarbon radical containing 7 to 11 carbon atoms, the sum of the carbon atoms in R' and R" is 13, and Z is a divalent radical of the structure

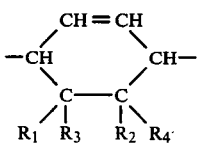

where $R_1$ and $R_2$ are H and $R_3$ and $R_4$ are H or

with the proviso that one of such radicals must be H and the other must be

from polyunsaturated monocarboxylic acid and acrylic acid using a crystalline clay mineral as catalyst.

BACKGROUND OF THE INVENTION

The above $C_{21}$ dicarboxylic acids are known in the art. The $C_{21}$ dicarboxylic acids are useful as surfactants, coatings and adhesives. Heretofore, the $C_{21}$ dicarboxylic acids have been prepared from linoleic acid generally from a tall oil fatty acid source by reacting the linoleic acid portion in a fatty acid mixture such as tall oil fatty acids and acrylic acid in the presence of an iodine catalyst. The process being carried out by reacting the linoleic acid portion in a fatty acid mixture with acrylic acid in an amount up to 26% by weight of fatty acids and with an iodine catalyst in an amount from 0.01% to 0.5% by weight of the fatty acids at a temperature between 200° C. and 270° C. The fatty acid dicarboxylic acid mixture is then separated by distillation into an oleic-type fatty acid and $C_{21}$ dicarboxylic acid.

Crystalline type clays have been used in dimerizing polyunsaturated monocarboxylic fatty acids. Typically, dimerization is accomplished by heating the polyunsaturated monocarboxylic fatty acids to a temperature of about 180° C. to 260° C.

SUMMARY OF THE INVENTION

It has been found that polyunsaturated monocarboxylic fatty acid containing eighteen carbon atoms react with acrylic acid in the presence of a crystalline type clay at a temperature between about 180° C. to 260° C. to form the above dicarboxylic acid containing twenty-one carbon atoms. The process is performed in one step, namely heating and stirring the clay, polyunsaturated monocarboxylic fatty acid and acrylic acid mixture in a closed vessel.

DETAILS OF THE INVENTION

The process of our invention consists of heating the mixed fatty acids derived from oils or fats whose unsaturated acid content consists predominately of polyunsaturated fatty acids with acrylic acid and small amounts of crystalline clay mineral and small amounts of water. The temperature of heating may range from about 180° C. to 260° C., with the preferred temperature being from about 220° C. to 250° C. The time of treatment is to a degree inversely proportional to the temperature and may range from as high as about 8 hours at the lower temperatures to as low as about 2 hours at the higher temperature and about 3 to 4 hours at the preferred temperature. The amount of clay employed is not particularly critical except that in the case of low quality acids, a quantity in excess of the minimum required may be needed to absorb color or other impurities. The amount may, therefore, range from about 1% by weight of the acids being reacted to as high a quantity as is economically sound practice, or 20% by weight of the acids being reacted.

No water is used in the process and that amount of water which may be used in the hydrolysis of any interester is subsequently liberated by further reaction. The quantity required is, therefore, small and may range from 1 to 5% by weight of the reaction mixture. Quantities in excess of 5% are not beneficial and, in fact, are somewhat harmful as excessive water greatly reduces the degree of reaction.

In general, all of the common commercial, abundant, crystalline, clay minerals may be used, such as: montmorillonite, kaolinite, hectorite, halloysite, attapulgite, sepialite. As a generality, clays vary considerably in composition, depending upon the locality of the deposit and other factors, and many of the commercial clays are mixtures of different chemical compounds. For instance, the commercial bentonites may be used in the practice of this process if they contain sufficient montmorillonite, say 75%. Commercial clays having lesser percentages of crystalline clay mineral may be employed, but it is the crystalline clay minerals which promote the reaction. While there may be rare crystalline clay minerals which cannot be used in this process, such clay minerals are not commercial products and are not mined for the market. All of the mined commercial crystalline clay minerals may be used in this process with good results. The bentonitic clays containing at least 75% montmorillonite are particularly recommended. Also the pH of the clay is preferably above 2 but below 7, and for best results the clay should have a pH in the neighborhood of 3 to 5. While more acid clays may be employed, their use tends to promote the formation of unsaponifiable components in the monomer. Best results are obtained when a lithiam ion is used with the clay. Preferably 0.50 meq Li+/g clay to 2 meq Li+/g clay is used. For optimum results a free radical inhibitor such a p-methoxyphenol is included in the reaction mixture.

Typical $C_{18}$ feed stocks for the use in the process of this invention include the fatty acids of linseed oil, safflower oil, soybean oil tall oil, cottonseed oil, corn oil, that is, the oils generally known as drying and semi-drying oils. Saturated acids or monounsaturated acids such as oleic acid which may be present do not interfere and are unchanged by the process. Polyunsaturated fatty acid means those fatty acids containing at least two double bond or ethylenic groups. It also includes fatty acids which contain more than two double bond or ethylene groups. If the groups are not conjugated initially, they become so during the process.

The process is carried out by introducing the requisite quantities of acids, clay and water into a vessel equipped with an agitator for maintaining the clay in suspension. Preferably about 1.25 to 3 moles (or one unsaturated equivalent) of acrylic acid are used per each mole of the polyunsaturated $C_{18}$ fatty acid containing a diene configuration in its chain (or one diene equivalent). The vessel is preferably closed and constructed to withstand the steam pressure which will be generated at the temperature employed. Alternatively, but less desirable, a vessel equipped with a reflux condenser to return the vaporized water may be employed. The charge is heated to the requisite temperature, preferably 220° C. to 250° C. and held at this temperature for a period of approximately 2 hours to 2.5 hours. The charge is then cooled and the pressure released to permit flashing of the water. The contents are then filtered to remove the earth and the filtrate subjected to a conventional fractional distillation to remove the nonpolymerized portion as distillate.

The following examples all involve the use of the general process just described. In these examples the iodine values were determined by the standard Wij's method. Colors were measured by the Gardner Standards of 1933. The acid equivalent weight and the saponfiication equivalent weight were run by standard methods. All quantities and proportions which are indicated in the foregoing description and in the following examples and claims are by weight.

EXAMPLE 1

To a 300 ml, stainless steel, magna-drive autoclave was added 168 g (0.3 diene eq.) tall oil fatty acid, 32.4 g (0.45 moles) glacial acrylic acid, 11.8 g (7% by weight of tall oil fatty acid) bentonite, 0.3 g (1% by weight of acrylic acid) p-methoxyphenol, and 0.3 g (0.75 meq. Li+/g clay) $Li_2CO_3$. The autoclave was sealed and purged with nitrogen gas three times. The reactants in the closed vessel were heated and stirred at 200° C. for 1 hour, then at 220° C. for 1 hour. Autogenic pressure after that time had risen to 60 psig and the reactants were cooled to room temperature and a sample was taken. The following day 12 g (0.167 moles) of acrylic acid was added to the autoclave and the contents reheated, with stirring, to 240° C. for about one hour. Autogenic pressure reached 298 psig. Then the reactants were cooled to room temperature. The autoclave contents were transferred to a pressure filter where the catalyst was removed. The dark colored filtrate was labeled. See Table I Sample 1 for analytical results.

EXAMPLE II

To the autoclave used in Example I was added 112 g (0.2 diene eq) tall oil fatty acids, 21.6 g (0.3 moles) glacial acrylic acid, 7.8 g (7% by weight of tall oil fatty acids) bentonite, and 0.44 g (1.5 meq Li+/g clay) $Li_2CO_3$. The vessel was sealed and flushed with nitrogen gas three times by evacuation. The evacuated vessel was heated, with stirring, at 225° C. to 235° C. for 2.25 hours, then at 205° C. for 65 hours. The reactor was cooled to 155° C. and vented. Maximum autogenic pressure was 109 psig at 203° C. The reaction mixture was pressure filtered yielding a dark, viscous liquid product. See Table I Sample 2 for analytical results.

EXAMPLE III

To the autoclave used in Example I was added 112 g (0.2 diene eq.) tall oil fatty acid, 28.8 g (0.4 moles) glacial acrylic acid, 7.8 g (7% by weight of tall oil fatty acid, bentonite, 0.29 g (1% by weight of acrylic acid) p-methoxyphenol, 0.44 g (1.5 meq Li+/g clay) $Li_2CO_3$, and 0.45 g (0.4% by weight of tall oil fatty acids) activation carbon. The autoclave was sealed and flushed three times with nitrogen. The sytem was left evacuated after the third nitrogen purge. The reactants were heated, with stirring, at 240° C. for 2.5 hours. The system pressure of 105 psig was attained at those conditions. The autoclave was vented at 154° C. and at 135° C. one millimeter of 85% $H_3PO_4$ was added to neutralize any soaps formed and as a filtration aid. The catalyst, carbon, and salts were removed by pressure filtration. The product was light yellow, clear crude $C_{21}$ diacid. See Table I and II, Sample 3 for analytical results.

EXAMPLE IV

Following the procedure of Example I, the process was conducted at 225° C. for 2.5 hours instead of 240° C. The maximum autogenic pressure of 37 psig was reached at the beginning of the heating cycle. The pressure dropped to a low of 30 psig at 225° C. midway through the run then climbed to 35 psig before cooling and initiated. The product was a clear, light colored crude $C_{21}$ diacid. At attached Table I and II Sample 4 for analytical results.

Table I

| | ANALYTICAL RESULTS | | | |
| --- | --- | --- | --- | --- |
| | Gas Liquid Chromotographic Results | | | |
| | Percentage of Product | | | |
| | SAMPLE | | | |
| Fraction | 1 | 2 | 3 | 4 |
| $C_{18}$ | 59.4 | 55.1 | 58.3 | 78.4 |
| Unknown | 8.1 | 10.0 | 5.2 | 4.2 |
| $C_{21}$ | 24.2 | 26.7 | 24.5 | 14.7 |
| $C_{36}$ | 8.3 | 9.2 | 12.0 | 2.4 |

Table II

| | Physical Measurements | | | | |
| --- | --- | --- | --- | --- | --- |
| | Acid eq. wt. | Saponification eq. wt. | Iodine value | Gardner color | Brookfield Visc. at 25° C. |
| Fatty Acid | 286.0 | 285.8 | 122.5 | 3+ | ca .3 poise |
| Crude $C_{21}$ diacid | 242.8 | 197.5 | 81.6 | 5+ | 3.95 poise |
| Crude $C_{21}$ diacid | 261.3 | 212.4 | 98.6 | 4+ | 1.3 poise |

The embodiments of the invention in which an exclusive property or privilege is claimed are defined as follows:

1. The method of preparing a dicarboxylic acid containing twenty-one carbon atoms having the structural formula

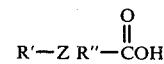

where R' is a monovalent straight chain aliphatic hydrocarbon radical containing 2 to 6 carbon atoms, R" is a divalent straight chain aliphatic hydrocarbon radical containing 7 to 11 carbon atoms, the sum of the carbon atoms is R' and R" is 13, and Z is a divalent radical of the structure

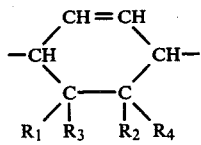

where $R_1$ and $R_2$ are H and $R_3$ and $R_4$ are H or

with the proviso that one of such radicals must be H and the other must be

from polyunsaturated monocarboxylic fatty acids containing eighteen carbon atoms comprising simultaneously reacting monocarboxylic polyunsaturated fatty acids with acrylic acid in a ratio of about 1.25 to 3 moles of acrylic acid to one diene equivalent of the polyunsaturated fatty acid in the presence of crystalline clay in an amount of about 1% to 20% by weight of the acids being reacted, said crystalline clay having a pH between about 2 to 7 and about 1% to 5% water by weight of the reaction mixture at a temperature between about 180° C. and 260° C. for a period of about 2 to 8 hours.

2. The process of claim 1 wherein the reaction temperature is between about 220° C. and 250° C.

3. The process of claim 1 wherein said polyunsaturated monocarboxylic fatty acids source is tall oil fatty acids.

4. The process of claim 1 wherein said crystalline clay mineral is bentonite.

* * * * *